United States Patent [19]

Aragon Reyes et al.

[11] Patent Number: 5,994,092
[45] Date of Patent: Nov. 30, 1999

[54] USE OF β-D-GALACTOPYRANOSYL-D-XYLOSES FOR THE PREPARATION OF COMPOSITIONS AND SOLUTIONS INTENDED TO THE EVALUATION OF INTESTINAL LACTASE, AND PRODUCTION PROCESS

[75] Inventors: Juan José Aragon Reyes; Francisco Javier Canada Vicinay; Alfonso Fernandez-Mayoralas Alvarez; Rosa Lopez Alvarez; Manuel Martin Lomas, all of Madrid, Spain; Daniel Villanueva Torregroza, Barranquilla, Colombia

[73] Assignees: Universidad Autonoma; Consejo Superior Investigaciones Cientificas, both of Madrid, Spain

[21] Appl. No.: 08/875,043

[22] PCT Filed: Nov. 8, 1996

[86] PCT No.: PCT/ES96/00208

§ 371 Date: Nov. 4, 1997

§ 102(e) Date: Nov. 4, 1997

[87] PCT Pub. No.: WO97/17464

PCT Pub. Date: May 15, 1997

[30] Foreign Application Priority Data

Nov. 8, 1995 [ES] Spain ..................................... 9502185

[51] Int. Cl.⁶ .............................. C12Q 1/54; C12Q 1/34; C12P 19/12; C12P 19/18
[52] U.S. Cl. ................................ 435/14; 435/18; 435/97; 435/99; 435/100
[58] Field of Search ................................. 435/100, 99, 97, 435/18, 14

[56] References Cited

FOREIGN PATENT DOCUMENTS 0 470 331   2/1992   European Pat. Off. ........ C12P 19/12

OTHER PUBLICATIONS

Rivera–Sagredo et al, Carb. Res. 228:129–135 (1992).
Lopez et al, Biotech. Letters. 13(10):705–710 (1991).
Gorin et al, Can. J. Chem. 42:2307–2317 (1964).
Toone et al, Tetrahedron 45(17):5397–5405 (1989).

*Primary Examiner*—Francisco Prats
*Attorney, Agent, or Firm*—Klauber & Jackson

[57] ABSTRACT

There is disclosed the use of O-β-D-galactopyranosyl-D-xyloses, particularly 2-O-β-D-galactopyranosyl-D-xylose and 3-O-β-D-galactopyranosyl-D-xylose, for the preparation of compositions and solutions intended to the evaluation of the intestinal lactase, which present an affinity to the substantially enchanced lactase. There is also disclosed a process for producing O-β-D-galactopyranosyl-D-xyloses, comprising: reacting a D-xylose and a substrate of β-D-galactopyranosyl in the presence of an enzyme β-galactosidase, in an aqueous medium buffered to a pH comprised between 5.0 and 9.0 and at temperature between 4 and 37° C., deactivating the β-galactosidase by heating at 100° C. when reaching the maximum yield of formation of disaccharides detected through thin layer chromatography, and isolating the formed disaccharides through filtration in a packed column with a thinner selected between water and water/alcohol.

6 Claims, 1 Drawing Sheet

USE OF β-D-GALACTOPYRANOSYL-D-XYLOSES FOR THE PREPARATION OF COMPOSITIONS AND SOLUTIONS INTENDED TO THE EVALUATION OF INTESTINAL LACTASE, AND PRODUCTION PROCESS

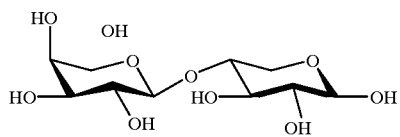

TECHNICAL SCOPE OF THE INVENTION

The deficiency or low activity in intestinal lactase which result in an insufficient or even zero capacity for digesting lactose, is rare as regards a congenital metabolical error, though it is a common syndrome in human adults. With the greater part of mammels, an acute decrease of the lactase activity exists from the moment of weaning. In humans with ancestors who have depended on a substantial consumption of milk or lacteous products during a long time, this decrease is less frequent. On the other hand, the deficiency or low activity in intestinal lactase is quite frequent in babies who are nursing.

The present invention is comprised in the field of bloodless evaluation methods of intestinal lactase acitivity.

BACKGROUND OF THE INVENTION

The determination of the intestinal lactose activity is of importance in paedriatrics and gastroenterology and may be directly carried out, parting from a mucous sample, or indirectly, parting from the level of glucose in the blood or from the expired hydrogen, after the administration of a dose to the individual.

The direct determination has the disadvantage of constituting a complex and expensive method since it requires specific instruments and very specialized personal for the technique of extraction of the sample which must be submitted to subsequent analysis, apart from its being disagreeable nad not lacking in danger to the individual.

The indirect determination has the advantage of being a technique involving blood, which requires the extraction of blood by a specialied person before the sample may be analyzed, apart from being complex and susceptible to errors, due to the existance of glucose originating from the digestion of other food taken by the individual, and of endogenous glucose which might have been mobilized.

Other methods of determination of the intestinal lactase are based on the fact that specific disaccharides are, based on their affinity to the lactase, subsceptible of acting as substrate of the lactase and transform, by the action of the enzyme, into specific monosaccharides which are absorbed easily by the intestine and eliminated through urine.

Thus, the methods disclosed in Spanish Patentes ES-P-478590 and ES-P-482073, are based on the evaluation "in vivo" by means of the oral administration of 3-O methyl lactase and the analysis of the 3-O-methyl-D-glucose in urine. However, said methods present the disadvantage that they require the employment of a chromatographic procedure for the detection of 3-O-methyl-D-glucose in urine, which implies complex and expensive facilites and analysis equipments.

On the other hand, in Spanish Patent ES-P-9001680 discloses the preparation of disaccharide 4-O-β-galactopyranosyl-D-xylose of formula (I)

for the evaluation of the intestinal lactase activity. Said disaccharide is administrated orally, it acts as substrate of the intestinal lactase and decomposes, in the intestinal tract, in xylose and galactose, absorbing the xylose and eliminating through urine where it may be directly evaluated by means of a simple colorimetric method. The disaccharide of Spanish Patent ES-P-9001680, presents the disadvantage that it presents, in spite of having a quite similar structure to that of the lactase, an enhanced affinity to the lactose. This implies that only a part of the digested 4-O-β-galactopyranosyl-D-xylose, is hydrolized based on the enzymatic activity of the lactase and, therefore, the non decomposed part in xylose and galacatose is eliminated with the feces. This implies a relatively substantial margin of error in view that the low or even non existant values of the xylose in the analyzed urine, may originate both from the deficient or zero intestinal lactase activity and from a deficient hydrolization of the disaccharide due to its lack of affinity to the lactase. In order to relieve said margin of errors, it is necessary that the individual digest a substantial quantity of disaccharides, which in turn may lead to intestinal problems such as diarrhea and the corresponding discomforts to the individual.

Spanish Patent ES-P-9001680 also discloses a method of preparation for the 4-O-β-galactopyranosyl-D-xylose, which basically comprises a synthesis parting from benzyl-β-D-xylopyranoside and which follows operational sequences which imply selective protection reactions, glycosylation and desprotection. Both the number of reaction stages, the use of expensive reactive agents such as silver triflate in the glyxosylation reaction, and the employment of chromatographic columns in the purification of intermediates and the final product, produce costs and present difficulties for the performance of said procedure at industrial scale.

On the other hand, Gorin et al. in "The Synthesis of β-Galacto- and β-Gluco-Pyranosyl disaccharides by "Sporobolomyces Singularis"", Can. J. Chem. 42(1964) 2307–2319, discloses the synthesis of a plurality of disaccharides, among which are the 2-O-δ-D-galactopyranosyl-D-xylose and the 3-O-δ-D-galactopyranosyl-D-xylose, by means of a purely experimental procedure. In this publication, the conclusion is reached that the products resulting form the transference of galactosyl, in the use of various acceptors, originate mainly more from the substitution of the secondary hydroxyl groups than from the primary hydroxyl groups, the minimum structural requirement for the reaction with an acceptor seeming to be the hydroxyl adjacent to the substituted hydroxyl group. However, in this publication, no use of the diverse synthetized disaccharides are disclosed.

DESCRIPTION OF THE INVENTION

In order to solve the disadvantages of the previously described state of the art, the object of the present invention is the use of β-D-galactopyranosyl-D-xyloses, specifically of 2-O-β-D-galactopyranosyl-D-xylose of the general formula (II)

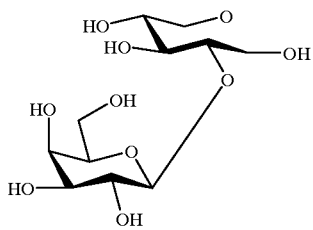

and of 3-O-β-D-galactopyranosyl-D-xylose, of the general formula (III)

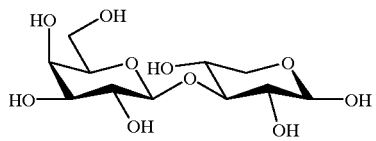

for the preparation of compositions and solutions used for the bloodless and reliable evaluation of intestinal lactase.

On the other hand, another object of the invention is a procedure which permits the preparation of the β-D-galactopyranosyl-D-xylose, the use of which is claimed, together with that of other β-D-galactopyranosyl-D-xylose, by means of a simplified method versus the conventional procedures of this type of disaccharides.

The β-D-galactopyranosyl-D-xyloses, that is to say, the 2-O-β-D-galactopyranosyl-D-xylose and the 3-O-β-D-galactopyranosyl-D-xylose the use of which is claimed, present an affinity to the lactase which is substantially enhanced versus the conventionally used disaccharides in this type of evaluations, which results to be surprising in view of the fact that both compounds are structurally less similar to lactase than the previously used compounds, such as the 4-O-β-galactopyranosyl-D-xylose, from which they are structurally differentiated by various hydroxyl groups respectively adjacent to the glycosydic bond in the molecule.

The disaccharides of formulas (II) and (III) may be included in compositions and solutions which are conventional in themselves, individually or jointly, or even mixed with a quantity of conventional dissacharides of formula (I) and/or with lower quantities of lactose. Such compositions and solutions may contain quantities of ingredients conventional in themselves, pharmaceutically acceptable, of at least one selected additive from among stabilizers, protectors, taste enhancers, lactose, gelifiants, fluxants and conservatives. The solutions may be water, aqueous or saline solutions which are conventional in themselves.

It has been observed that even when a mixture of the three disaccharides (I), (II), and (III) is used, the evaluation of the intestinal lactase activity, through the xylose present in the eliminated urine, results substantially enhanced versus the possibilitated evaluation when only disaccharide (I) is administered, which clearly demonstrates the surprising effect inherent to the invention.

The procedure, according to the invention, includes the possibility of preparing β-D-galactopyranosyl-D-xylose which includes the previously indicated disaccharides I, II and III, and comprises the following stages: React a D-xylose and a substrate of β-D-galactopyranoside in the presence of a β-galactosidase enzyme, according to the drawing of the reaction

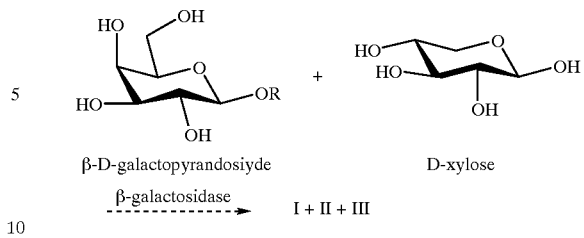

the concentration of D-xylose being from 2 to 20 times over that of the β-D-galactopyranoside, in an aqueous medium buffered to a pH of 5,0–9,0 and at a temperature comprised between 4 and 37° C.; desactivate the β-galactosydose, by heating at 100° C. when reaching the maximum yield of formation of disaccharides detected (normally after 4 to 8 hours) by means of thin layer chromatography or with an active carbon column, and isolation of the formed disaccharides through filtration in a packed column with a thinner selected between water or water/alcohol, thus obtaining a mixture of disaccharides (I), (II), and (III) which may be included in compositions or solutions both as mixtures of the three disaccharides, or as mixture, after the corresponding isolation of one of the disaccharides (II) or (III) with disaccharide (I), or individually.

In an embodiment of the procedure, the β-D-galactopyranoside used is O-nitrophenyl, β-D-galactopyranoside while in another embodiment it is lactose.

On the other hand, the β-galactosidase may be for example, the *Escherichia Coli,* as commercialized by Spanish Company SIGMA-ALDRICH QUÍMICA, S.A.

The procedure may be conducted in the presence of cosolvents miscible in water, such as acetonitrile, dimethyl formamide or dimethyl sulfoxide.

The filtration columns employed for the isolation of the disaccharides may be packed with Sephadex™ G-10 or Biogel™ P2, or else with active carbon.

Disaccharides II and III may also be obtained through other conventional methods, such as those disclosed by Gorin et al. in "The Synthesis of β-Galacto And β-Gluco-Pyranosyl disaccharides by *Sporobolomyces Singilaris*", Can. J. Chem. 42(1964) 2307–2319.

BRIEF DESCRIPTION OF THE FIGURE

The only FIGURE is a graphic representation of the evolution of a) the hydrolysis in vivo, of a mixture of the β-D-galactopyranosyl-D-xylose (I), (II) and (III) as a percentage of xylose eliminated through urine and b) the intestinal lactase activity (nm/min/mg protein) during the growth of rats as described in the examples

EMBODIMENT OF THE INVENTION

Figure 1:
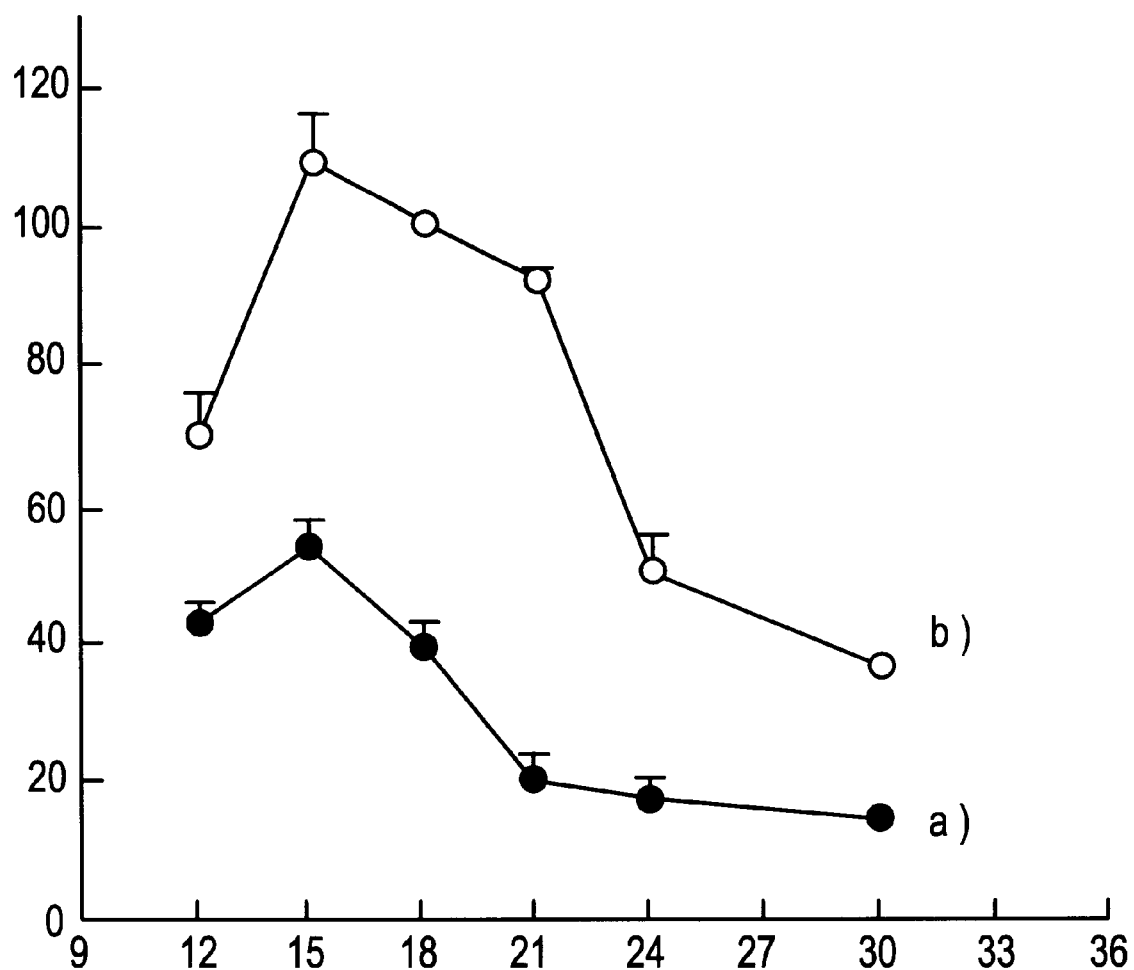

The following examples describe with illustrative, though non limitative character, relevant aspects of the invention.

EXAMPLE 1

Preparation of a Mixture of 4-O-β-D-galactopyranosyl-D-xylose (Disaccharide I), 2-O-β-D-galactopyranosyl-D-xylose (Disaccharide II) and 3-O-β-D-galactopyranosyl-D-xylose (Disaccharide III)

To a solution of σ-nitrophenyl β-galactopyranoside (4 g, 50 mM) and xylose (20 g, 500 nM), in buffered water (0,05 M $KH_2PO_4$, 1 mM $MgCl_2$, 5 mM mercapto ethanol, 265 mL, pH 7,0), was added β-galactosidase of *E. Coli* of SIGMA (1,5 mg, 560 U), and the mixture was incubated at 25° C.

during 5 hours and 45 min. After this time had elapsed, the mixture was heated at 100° C. during 10 min., it concentrated and the resultant residue was introduced into a column of activated carbon using a gradient of water-ethanol 1:0→85:15. First the monosaccharides xylose and galactose were eluated, and next the mixture of the disaccharides I, II and III, obtaining 2 g of the mixture of disaccharides (50% in relation to the equivalents of the initial σ-nitrophenyl β-galactopyranoside), in a ratio I:II:III of 8,6:1,4:1,0 respectively.

Of the different functions the disaccharides I, II and III comprise, some were separated, with each one of them pure, which were used to characterize them by RNM. The 'H-RMN spectrum (300 MHz, $D_2O$), measured with a Varian XL-300 spectometer, of the fractions with disaccharide I, was identical to that of the previously prepared product.

With the object of characterizing and determining unequivocally, the regio-chemistry of the bond formed in disaccharides II and III, the fractions enriched in said compounds were acetylized and the resultant products were isolated by a semipreparation HPLC (normal phase column $SiO^2$, ethyl hexane-acetate 1:1, detection by refraction index). Subsequently, the 'HRMN spectrum (300 MHz, $CDL_3$) of each one of the obtained derivates was recorded:

Acetylated derivate of 2-O-β-D-galactopyranosyl-σ-D.xylopyranose.

Acetylated derivate of 2-O-β-D-galactopyranosyl-β-D-xylopyranose.

Acetylated derivate of 3-O-β-D-galactopyranosyl-σ-D-xylopyranose.

Acetylated derivate of 3-O-β-D-galactopyranosyl-β-D-xylopyranose.

The ratio of disaccharides I, II and III obtained in the chromatographic column was determined by gas chromatography with a chromatograph equipped with a flame ionization detector and capilar column SE-54 (stationary phase: 5% diphenyl and 95% dimethyl polysyloxane, 15 m length, 0,15 mm inside diameter, and μm thickness). In the analysis, a nitrogen flow of 1 mL/min was used. The temperature programmes used were: initial temperature 160° C.; initial time 2 min; temperature increase 5° C./min; final temperature: 250° C. The samples were analysed after trimethyl sylication by means of the following protocol: an aliquote (10 μl) was heated at 100° C. during 10 min, after which, pyridine was added (25 μL) which contained as internal reference benzyl β--xylopyranoside (10 mM) and N-trimethyl sylimidazol (25 μL), continuing heating at 60° C. during 30 min. The retention times of the peaks assignable to the different disaccharides were as follows;

Benzyl β--xylopyranoside (internal reference): 12,04 min
disdaccharide I: 20,35 and 20,50 min
disaccharide II: 18,46 and 19,50 min
disaccahride III: 18,30 min

EXAMPLE 2

Kinetic Test of the In Vitro Hydrolization

Disaccharides I, II and III and lactose were hydrolized according to the method of A. Rivera-Sagredo, F. J. Cañada, O. Nieto, J. Jiménez-Barbero and M. Martín-Lomas, Eur. J.Biochem., 209 (1992) 415–422, with intestinal lactase of a sheep at pH 6.0, with the following results, in relation to constants of Michaelis ($K_m$) and maximum rates ($V_{max}$):

| Disaccharide | $K_m$ (mM) | $V_{max}$ (%) |
|---|---|---|
| lactose | 11.0 | 100 |
| disaccharide I | 340.0 | 20 |
| disaccharide II | 14.0 | 20 |
| disaccharide III | 4.0 | 70 |

It may be observed that the Michaelis constants of disaccharides II and III are substancially lower that of disaccharide I, the $K_m$ of disaccharide III being even lower than that of the lactose, which makes evident an extraordinary affinity of disaccharides II and III to the lactase.

EXAMPLE 3

Elimination of Xylose in Urine After Oral Administration of a Mixture of disaccharides I, II and III A mixture of disaccharides I, II and III (in a ratio of 8,6:1,4:1,0 respectively) prepared through the procedure of example 1, was employed to evaluate the activity of intestinal lactase. For this, a group of 17 Spraque-Dawley nursing rats from the same litter and with 12 days of age, were kept without eating during 6 hours separated from their mother. After said time had elapsed, the basal urine of each animal was collected by means of vesical transabdominal pressure and immediately 18,2 mg of the diluted disaccharide mixture in0,3 mL of distilled water was administered to each, using an intragastrical stylet. As from this moment, urine was collected during the following 5 hours, determining in the same, the xylose eliminated by means of colorimetric analysis based on the fluoroglucinol reaction, and using the basal urine as target. Immediately after the collection of the urine, three of the animals on which the lactase activity in the intestinal mucous was directly determined, were sacrificed. For this, a section of small intestine was dried and washed, the mucous collected by means of scraping with glass and homogenized, measuring the lactase activity spectrophotometrically in the homogenized product. The remaining animals were returned to the mother and the experiment repeated with them under similar conditions after 15, 18, 21, 24 and 30 days after which, the litter was extinguished. The resulting mean values of said experiment are included in the FIGURE, in which is reflected, the hydrolysis of the disaccharides I, II and III mixture in vivo, and the intestinal lactase activity during the growth of the rat. To achieve this, the elimination xylose (%) [curve a)] is represented, together with the lactase activity (nm/min/mg protein) [curve b)] versus age (in days). The results of this experience indicates: 1) That the presence of xylose in urine is detected, coming from the hydrolysis of the disaccharides administered by the action of the intestinal lactase; and 2) That the course of elimination of xylose in urine, originated by the oral administration, runs parallel to the known physiological modification of the intestinal lactase activity which declines throughout the length of the individual's development. Said experience demonstrates that the methodology is useful for the evaluation "in vivo" of the intestinal lactase activity, the procedure being employed for the evaluation of said activity, in a bloodless manner, with diagnostical ends, which has particular applicability in nursing individuals in which the existence of a deficiency of said enzyme is suspected.

EXAMPLE 4

A group of Sprague-Dawley nursing rats of the same litter and with 15 days of age, were kept without eating during four hours in metabolical boxes at 30° C. Each one of them was administered 18.2 g of disaccharide I in 0.5 ml of distilled water. Urine was collected from the animals, pressing the bladder transabdominally during 5 hours. The xylose eliminated through the urine during this time was evaluated spectroscopically. The elimination of xylose resulted to be of 21%, that is to say, less than half than the result of the mixture of products I, II and III after 15 days.

By comparing the data from this example with those of example 3, it is evident that the "in vivo" affinities of disaccharides II and III are so high that they even compensate the worst affinity of disaccharide I, when the three disaccharides are administered in a mixture in which disdaccharide I prevails.

We claim:

1. A method for evaluating intestinal lactase, the method comprising orally administering a mixture of β-D-galactopyranosyl-D-xylose disaccharides comprising a xylose moiety linked by a glycosidic bond to a galactose moiety to a human individual, collecting a urine sample from the individual, and determining the xylose contents in the sample, wherein the mixture comprises at least one β-D-galactopyranosyl-D-xylose having two hydroxyl groups adjacent respectively to the glycosidic bond in the xylose moiety, and 4-β-D-galactopyranosyl-D-xylose.

2. A method according to claim 1, wherein the β-D-galactopyranosyl-D-xylose having two hydroxyl groups adjacent respectively to the glycosidic bond in the xylose moiety is selected from 2-O-β-D-galactopyranosyl-D-xylose, 3-O-β-D-galactopyranosyl-D-xylose and mixture thereof.

3. A method according to claim 1 or 2, wherein the β-D-galactopyranosyl-D-xylose are comprised in a composition comprising pharmaceutically acceptable amounts of at least one additive selected form the group consisting of stabilizers, taste improving agents, lactose, gel forming agents and preservatives.

4. A method according to claim 1, wherein the dissacharides are present in aqueous solution.

5. A method according to claim 4, wherein the solution is an aqueous saline solution.

6. A method according to claim 1, wherein β-D-galactopyranosyl-D-xyloses are comprised in a solution comprising pharmaceutically acceptable amounts of at least one additive selected from the group consisting of stabilizers, taste improving agents, lactose and preservatives.

* * * * *